US00PP29008P2

(12) United States Plant Patent
Berry

(10) Patent No.: US PP29,008 P2
(45) Date of Patent: Feb. 27, 2018

(54) ***GARDENIA* PLANT NAMED 'PS-2013-4'**

(50) Latin Name: *Gardenia jasminoides*
Varietal Denomination: PS-2013-4

(71) Applicant: Capstone Plants Inc., Grand Saline, TX (US)

(72) Inventor: James B. Berry, Edgewood, TX (US)

(73) Assignee: CAPSTONE PLANTS, INC., Grand Saline, TX (US)

( * ) Notice: Subject to any disclaimer, the term of this patent is extended or adjusted under 35 U.S.C. 154(b) by 0 days.

(21) Appl. No.: 14/999,966

(22) Filed: Jul. 20, 2016

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Anne M Grunberg
(74) *Attorney, Agent, or Firm* — Penny J Aguirre

(57) ABSTRACT

A new cultivar of *Gardenia* named 'PS-2013-4', that is characterized by its compact plant habit that is equal in height and width, its dense self-branching plant habit without pruning, its double flowers that bloom in late spring with two full spring cycles under ideal conditions followed by spot blooming through the fall, its cold hardiness at least to U.S.D.A. Zone 7 with no winter foliage freezing, and its good resistance to root rot.

2 Drawing Sheets

Botanical classification: *Gardenia jasminoides*.
Variety denomination: 'PS-2013-4'.

BACKGROUND OF THE INVENTION

The present invention relates to a new and distinct cultivar of *Gardenia jasminoides*. The new cultivar will be referred to hereafter by its cultivar name, 'PS-2013-4'. 'PS-2013-4' is a new cultivar of *Gardenia* grown for use as a landscape shrub.

The new cultivar of *Gardenia* is a selection from a controlled breeding program conducted by the Inventor in Grand Saline, Tex. The objectives of the breeding program are to create new *Gardenia* cultivars with good foliage cold hardiness, floriferous blooming habits, glossy green foliage, and compact plant habits.

'PS-2013-4' originated from open pollination of an unnamed and unpatented plant of *Gardenia jasminoides* plant from the Inventor's breeding program in May of 2011. The male parentage is therefore unknown. 'PS-2013-4' was selected as a single unique plant in May of 2013 from amongst the resulting seedlings.

Asexual propagation of the new cultivar was first accomplished by semi-hardwood stem cuttings under the direction of the Inventor in Grand Saline, Tex. in July of 2013. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PS-2013-4' as a new and unique cultivar of *Gardenia*.

1. 'PS-2013-4' exhibits a compact plant habit that is equal in height and width.

2. 'PS-2013-4' exhibits a dense self-branching plant habit without pruning.
3. 'PS-2013-4' exhibits double white flowers that bloom in late spring with two full spring cycles under ideal conditions followed by spot blooming through the fall.
4. 'PS-2013-4' exhibits glossy dark green foliage.
5. 'PS-2013-4' exhibits cold hardiness at least to U.S.D.A. Zone 7 with no winter foliage freezing.
6. 'PS-2013-4' exhibits good resistance to root rot.

The female parent of 'PS-2013-4' differs from 'PS-2013-4' in having a plant habit that is taller than it is wide, in having a less floriferous blooming habit, and in having fewer leaves per stem. 'PS-2013-4' can be most closely compared to the *Gardenia jasminoides* cultivars 'Whispering Pines' (not patented) and 'Double Mint' (U.S. Plant Pat. No. 23,507). 'Whispering Pines' is similar to 'PS-2013-4' in being resistant to root rot and in having a bloom season that begins in the spring followed by spot blooming through the fall. 'Whispering Pines' differs from 'PS-2013-4' in having leaves that are larger in size and in having an open growth habit that is not self-branching. 'Double Mint' is similar to 'PS-2013-4' in being having double flowers and in having a similar plant size that is equal in height and width. 'Double Mint' differs from 'PS-2013-4' in having leaves that are shorter in length, in having leaves with more rounded apices, and in having dull green foliage.

BRIEF DESCRIPTION OF THE DRAWINGS

The accompanying colored photographs illustrate the overall appearance and distinct characteristics of the new *Gardenia*. The photographs were taken of a 1 year-old plant as grown outdoors in a two-gallon container in Grand Saline, Tex.

The photograph in FIG. 1 provides a side view of the plant habit of 'PS-2013-4'.

Figure 1:
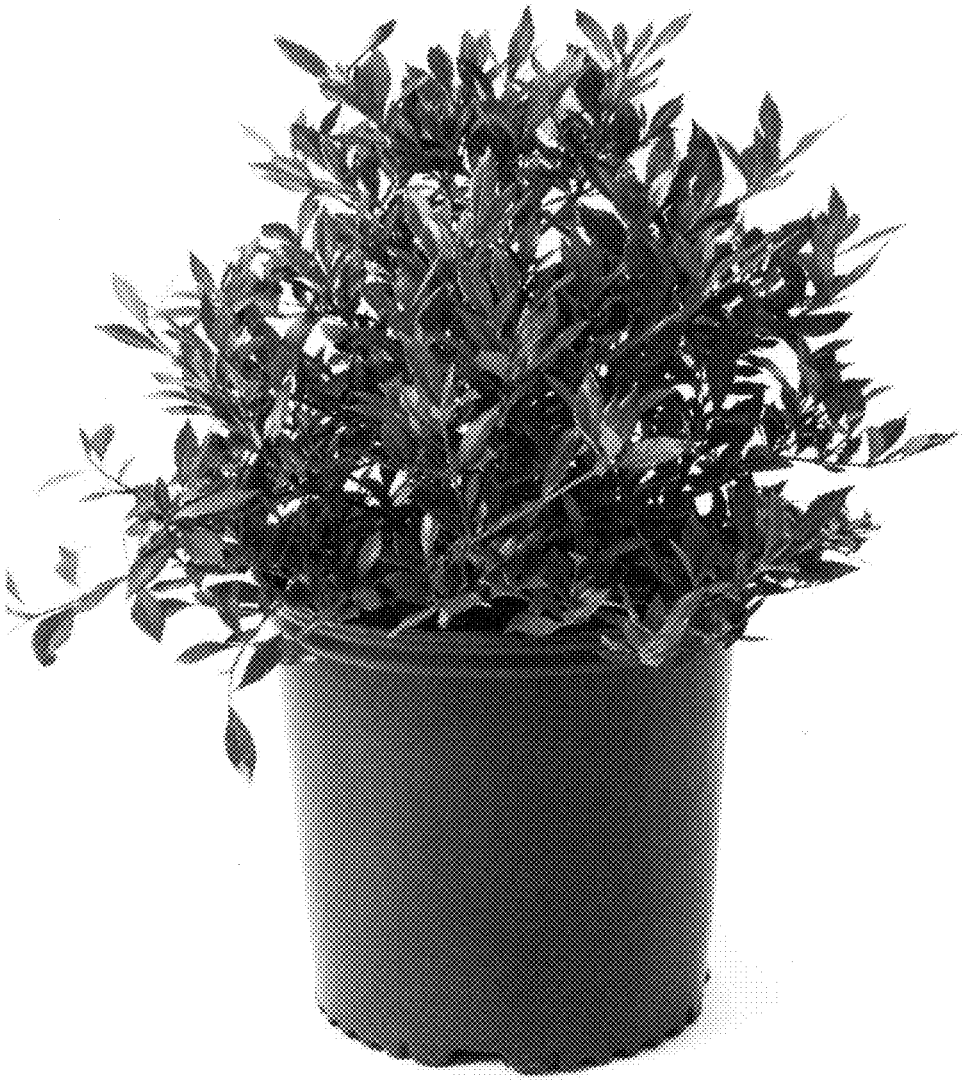
Figure 2:
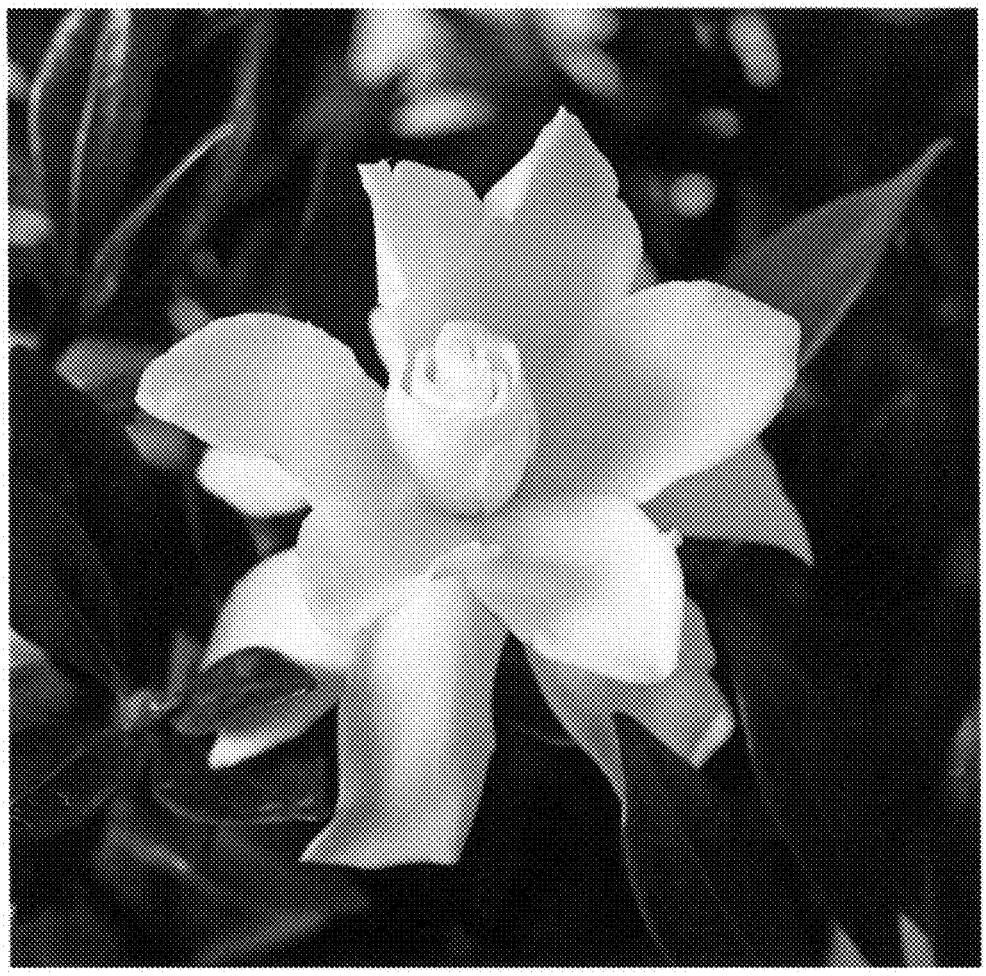

The photograph in FIG. 2 provides a close-up view of a flower of 'PS-2013-4'.

The colors in the photographs are as close as possible with the photographic and printing technology utilized and the color values cited in the detailed botanical description accurately describe the colors of the new *Gardenia*.

DETAILED BOTANICAL DESCRIPTION

The following is a detailed description of 1 year-old plants of the new cultivar as grown outdoors in two-gallon containers in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit.*—Four weeks in late spring (with two full spring cycles under ideal conditions) followed by spot flowering through fall in Grand Saline, Tex.

*Plant type.*—Evergreen shrub.

*Plant habit.*—Compact and very densely branched.

*Height and spread.*—An average of 91 cm in height and width as a mature plant in the landscape.

*Cold hardiness.*—At least to U.S.D.A. Zone 7.

*Diseases and pests.*—Good resistance to root rot (*Phytophthora* spp.) has been observed.

*Propagation.*—Semi-hardwood stem cuttings.

*Growth rate.*—Vigorous.

*Root description.*—Fibrous roots, 160A to 165A in color.

*Root development.*—About 7 weeks to root and 18 months to finish in a 3-gallon container.

Branch description:

*Stem color.*—Young; 143A, maturing; 137A with woody striations of 148A, mature wood; 199A and 200A and 138B.

*Stem surface.*—Young; glabrous and shiny, maturing; striated with woody streaks, mature wood; moderately coarse bark.

*Branching.*—10 lateral branches emerging from base, an average of 3 to 5 secondary branches per lateral branch.

*Internode length.*—Variable, up to 5 cm.

*Stem size.*—Lateral branches; an average of 22 cm in length and 5 mm in width, secondary branches; up to 5 cm in length and 3 mm in width.

*Stipules.*—Broadly elliptic in shape, 2 fused into sheath above leaf attachment, base truncate, an average of 8 3 mm in length and width, membranous surface, color 165A and somewhat translucent.

Foliage description:

*Leaf type.*—Simple.

*Leaf shape.*—Lanceolate.

*Leaf apex.*—Acuminate.

*Leaf base.*—Attenuate.

*Leaf arrangement.*—Whorls and opposite.

*Leaf venation.*—Pinnate, not conspicuous, color matches leaf coloration on upper and lower surface, center vein upper and lower surface N144A in color.

*Leaf size.*—Average of 7 cm in length and 2 cm in width.

*Leaf fragrance.*—None.

*Leaf color.*—Young upper and lower surface; 144A, mature upper surface; NN137A, mature lower surface; 146B.

*Leaf number.*—An average of 46 per lateral branch.

*Leaf surface.*—Shiny and glabrous on upper surface and glabrous and dull on lower surface.

*Leaf substance.*—Thick.

*Petioles.*—Short, an average of 4 mm in length and 3 mm in diameter, color 144A, surface glabrous and shiny.

Inflorescence description:

*Inflorescence type.*—Solitary flowers from upper leaf axils.

*Flower number.*—An average of 3 to 4 per lateral branch (at different stages of opening).

*Flower fragrance.*—Strong, pleasant fragrance typical for *Gardenia*.

*Flower longevity.*—An average of 5 to 7 days, depending on temperature.

*Flower type.*—Salviform with double rotate lobes (rose-like appearance).

*Flower size.*—An average of 5.7 cm in diameter and 4 cm in depth, including corolla tube.

*Flower buds.*—Conical in shape, an average of 2 cm in length and 1 cm in width, prior to opening, a blend between 10D and N144B in color, held in an upright to slightly drooping angle, glabrous, shiny surface.

*Corolla lobes.*—About 20 per flower, an average of 2.5 cm in length and 1.7 cm in width, 25% to 50% overlapping in a whorl, obovate in shape, rounded apex, entire margins that are slightly rolled downwards, base is fused into the corolla tube, upper and lower surface is satiny, smooth, and velvety, color; upper and lower surface when opening and fully open NN155B with lower outer petals suffused with a blend between 144A and N144B around the margin, when mature and fading: a blend of 10A to 10D.

*Corolla tube.*—An average of 1.2 cm in length and 5 mm in width, glossy, smooth, satiny surface, color 144D.

*Calyx.*—An average of 3 cm in length and 1 cm in diameter, glabrous, shiny surface, an average of 6 ridges form the calyx, a blend of 143A and 144B in color.

*Sepals.*—An average of 6, 50% fused to calyx, star shaped en masse, both sides of sepal fused together to appear flattened in shape, pointed apex, glabrous surface, up to 1.5 cm in length and 3 mm in width, a blend of 144A in color.

*Peduncles.*—Oval in shape, an average of 1 cm in length and 3 mm in diameter, glossy and glabrous surface, 144A in color.

Reproductive organs:

*Gynoecium.*—1 pistil, stigma is prominent, obelliptic in shape, and 10B in color, style; an average of 1 cm in length and 6 mm in diameter, 10D in color, ovary; 2-carpellate, 5 mm in length and 2 mm in width, oblong in shape, 11D in color, numerous shiny ovules.

*Androecium.*—An average of 6 stamens, filaments are adnate to inner corolla, an average of 7 mm in length, and 174A in color, anthers; an average of 1 mm in length, 177A in color, pollen is abundant in quantity and 14C in color.

It is claimed:

1. A new and distinct cultivar of *Gardenia* plant named 'PS-2013-4' as herein illustrated and described.

* * * * *